(12) United States Patent
Franzen et al.

(10) Patent No.: US 7,929,141 B2
(45) Date of Patent: Apr. 19, 2011

(54) SENSOR AND METHOD OF DETECTING THE CONDITION OF A TURF GRASS

(75) Inventors: David Franzen, Lincoln, NE (US); John Rada, Ceresco, NE (US); Kevin Ediger, Lincoln, NE (US); Gregory L Biggs, Lincoln, NE (US); Jonathan M. Welles, Lincoln, NE (US); Tanvir Demetriades-Shah, Lincoln, NE (US)

(73) Assignee: Li-Cor, Inc., Lincoln, NE (US)

( * ) Notice: Subject to any disclaimer, the term of this patent is extended or adjusted under 35 U.S.C. 154(b) by 214 days.

(21) Appl. No.: 12/008,402

(22) Filed: Jan. 10, 2008

(65) Prior Publication Data
US 2008/0316491 A1 Dec. 25, 2008

(51) Int. Cl.
*G01N 21/55* (2006.01)
(52) U.S. Cl. ........................................................ 356/445
(58) Field of Classification Search .................. None
See application file for complete search history.

(56) References Cited

U.S. PATENT DOCUMENTS

| | | |
|---|---|---|
| 2,514,405 A | 7/1950 | Marihart |
| 2,682,132 A | 6/1954 | Marihart |
| 2,894,178 A | 7/1959 | Chesebrough et al. |
| 3,373,870 A | 3/1968 | Black et al. |
| 3,488,511 A | 1/1970 | Mori et al. |
| 3,512,587 A | 5/1970 | Shader |
| 3,590,925 A | 7/1971 | Troutner et al. |
| 3,609,913 A | 10/1971 | Rose |
| 3,652,844 A | 3/1972 | Scott, Jr. |
| 3,701,218 A | 10/1972 | Priest |
| 3,821,550 A | 6/1974 | Priest |
| 3,881,568 A | 5/1975 | Ando et al. |
| 3,910,701 A | 10/1975 | Henderson et al. |
| 4,013,875 A | 3/1977 | McGlynn |
| 4,015,366 A | 4/1977 | Hall, III |

(Continued)

FOREIGN PATENT DOCUMENTS

DE   23127   12/1985

(Continued)

OTHER PUBLICATIONS

Alsip et al., "Computer Correlation of Soil Color Sensing With Positioning for Application of Fertilizer and Chemicals", *Automated Agriculture for the Proceeding of the 1991 Symposium*, 5 pages, 1991.

(Continued)

*Primary Examiner* — Gregory J Toatley, Jr.
*Assistant Examiner* — Juan D Valentin
(74) *Attorney, Agent, or Firm* — Kilpatrick Townsend & Stockton LLP

(57) ABSTRACT

A method of detecting the condition of a turf grass is described. According to one aspect of the invention, the method comprises steps of attaching an active sensor to a mower; traversing a section of turf grass; and processing the output of the sensor. A device for detecting the condition of turf grass is also disclosed. The device comprises an array of illuminating devices generating a pattern of illuminating light; a detecting device receiving a pattern of reflected light which is coincident with the pattern of illuminating light; a detecting device adapted to detect stray light from the array of illuminating devices; and a feedback loop controlling the array of illuminating devices. A system employing the device is also disclosed.

1 Claim, 11 Drawing Sheets

U.S. PATENT DOCUMENTS

| | | | |
|---|---|---|---|
| 4,029,391 A | 6/1977 | French | |
| 4,092,800 A | 6/1978 | Wayland, Jr. et al. | |
| 4,133,404 A | 1/1979 | Griffin | |
| 4,179,216 A | 12/1979 | Theurer et al. | |
| 4,206,569 A | 6/1980 | Randolph | |
| 4,354,339 A | 10/1982 | Nokes | |
| 4,369,886 A | 1/1983 | Lane et al. | |
| 4,443,866 A | 4/1984 | Burgiss, Sr. | |
| 4,482,960 A | 11/1984 | Pryor | |
| 4,527,897 A | 7/1985 | Okabe | |
| 4,550,526 A | 11/1985 | Smucker | |
| 4,558,786 A | 12/1985 | Lane | |
| 4,573,547 A | 3/1986 | Yoshimura et al. | |
| 4,618,257 A | 10/1986 | Bayne et al. | |
| 4,626,993 A | 12/1986 | Okuyama et al. | |
| 4,628,454 A | 12/1986 | Ito | |
| 4,630,773 A | 12/1986 | Ortlip | |
| 4,674,048 A | 6/1987 | Okumura | |
| 4,699,273 A | 10/1987 | Suggi-Kiverani et al. | |
| 4,709,265 A | 11/1987 | Silverman et al. | |
| 4,709,505 A | 12/1987 | Lempa, Jr. | |
| 4,727,475 A | 2/1988 | Kiremidjian | |
| 4,744,207 A | 5/1988 | Hanley et al. | |
| 4,768,713 A | 9/1988 | Roper | |
| 4,768,715 A | 9/1988 | Sali et al. | |
| 4,777,785 A | 10/1988 | Rafaels | |
| 4,878,598 A | 11/1989 | Ruschhaupt, Jr. | |
| 4,991,341 A | 2/1991 | Douglas | |
| 4,994,970 A | 2/1991 | Noji et al. | |
| 5,015,868 A | 5/1991 | Park | |
| 5,021,645 A | 6/1991 | Satula et al. | |
| 5,033,397 A | 7/1991 | Colburn, Jr. | |
| 5,050,771 A | 9/1991 | Hanson et al. | |
| 5,068,540 A | 11/1991 | Tsuji | |
| 5,072,128 A | 12/1991 | Hayano et al. | |
| 5,109,161 A | 4/1992 | Horiuchi et al. | |
| 5,144,767 A | 9/1992 | McCloy et al. | |
| 5,204,669 A | 4/1993 | Dorfe et al. | |
| 5,222,324 A | 6/1993 | O'Neall et al. | |
| 5,237,386 A | 8/1993 | Harley | |
| 5,278,423 A | 1/1994 | Wangler et al. | |
| 5,296,702 A | 3/1994 | Beck et al. | |
| 5,319,196 A | 6/1994 | Cleven | |
| 5,386,285 A | 1/1995 | Asayama | |
| 5,389,781 A | 2/1995 | Beck et al. | |
| 5,438,817 A | 8/1995 | Nakamura | |
| 5,507,115 A | 4/1996 | Nelson | |
| 5,520,333 A | 5/1996 | Tofte | |
| 5,567,947 A | 10/1996 | Kebabian | |
| 5,585,626 A | 12/1996 | Beck et al. | |
| 5,636,342 A | 6/1997 | Jeffries | |
| 5,673,637 A | 10/1997 | Colburn, Jr. et al. | |
| 5,704,546 A | 1/1998 | Henderson et al. | |
| 5,763,873 A | 6/1998 | Beck et al. | |
| 5,789,741 A | 8/1998 | Kinter et al. | |
| 5,793,035 A | 8/1998 | Beck et al. | |
| 5,809,440 A | 9/1998 | Beck et al. | |
| 5,833,144 A | 11/1998 | Kinter | |
| 5,837,997 A | 11/1998 | Beck et al. | |
| 5,884,224 A | 3/1999 | McNabb et al. | |
| 5,938,704 A | 8/1999 | Torii | |
| 6,062,496 A | 5/2000 | Kinter | |
| 6,138,590 A | 10/2000 | Colburn, Jr. | |
| 6,160,902 A | 12/2000 | Dickson et al. | |
| 6,393,927 B1 | 5/2002 | Biggs et al. | |
| 6,466,321 B1 * | 10/2002 | Satake et al. | 356/402 |
| 6,596,996 B1 | 7/2003 | Stone et al. | |
| 6,601,341 B2 | 8/2003 | Raun et al. | |
| 6,681,163 B2 | 1/2004 | Stam et al. | |
| 6,813,544 B2 | 11/2004 | Hood et al. | |
| 6,880,291 B2 | 4/2005 | Raun et al. | |
| 6,907,319 B2 | 6/2005 | Hoelscher et al. | |
| 7,188,450 B2 | 3/2007 | Raun et al. | |
| 2002/0169558 A1 | 11/2002 | Smith et al. | |
| 2004/0065834 A1 | 4/2004 | Stone et al. | |

FOREIGN PATENT DOCUMENTS

| | | |
|---|---|---|
| GB | 590598 | 7/1947 |
| GB | 2 200 446 A | 8/1988 |
| NZ | 229625 | 5/1991 |
| SU | 203340 | 7/1967 |
| SU | 382367 | 8/1973 |
| SU | 471074 | 8/1975 |
| SU | 547183 | 4/1977 |
| WO | WO 03/010521 | 2/2003 |

OTHER PUBLICATIONS

Barton, "A New Age of Weed Control", "The Grower", pp. 20 and 24, Feb. 1993.

Bell, Ph.D. et al., "A Futuristic Technique for Turf Management", *Golf Course Management*, pp. 73-75, Aug. 2001.

Bell et al., "Vehicle-Mounted Optical Sensing: An Objective Means for Evaluating Turf Quality", *Crop Science*, vol. 42, pp. 197-201, Jan.-Feb. 2002.

Bell, et al., "Turf Area Mapping Using Vehicle-Mounted Optical Sensors", http://crop.scijournals.org/cgi/content/abstract/42/2/648, pp. 1-2, 2002.

Burchfield, "Mower Innovations", http://grounds-mag.com/ar/grounds_maintenance_mower_innovations/, pp. 1-7, May 2001.

"Crop Circle Evaluation Package", Holland Scientific, 1 page, 2004.

"Crop Circle", Holland Scientific, 1 page, 2004.

Felton et al., "A Microprocessor Controlled Technology to Selectively Spot Spray Weeds", *Automated Agriculture for the Processing of the 1991 Symposium*, 4 pages, 1991.

Felton et al., "A Microprocessor Controlled Technology to Selectively Spot Spray Weeds", 5 pages, 1991.

Fermanian et al., "Precision Turfgrass Management", *1999 Illinois Turfgrass Research Report*, pp. 10-13, 1999.

"Futuristic Trends for Turfgrass Management", http://www.ncga.org/turf/turf4.htm, pp. 1-2, printed on Nov. 30, 2004.

"Green Seekers- NTech: A Brief History", http://www.greenseeker.com/company_hist.html, pp. 1-2, 2001.

"GreenSeeker Frequently Asked Questions", http://www.ntechindustries.com/greenseeker_faqs.html, pp. 1-6, 2003.

"Greenseeker Manual Downloads", http://www.ntechindustries.com/greenseeker-manuals.html, pp. 1, 2003.

"Holland Scientific- Pioneering New Technologies for a New Millenia," "New from Holland Scientific," http://www.hollandandscientific.com/products.htm , pp. 1, 2004.

"Holland Scientific- Pioneering New Technologies for a New Millenia," "What's New from Holland Scientific," http://www.hollandscientific.com/new.htm pp. 1, 2004.

"Is Precision Management on Golf Courses Feasible?", 15 pages, Apr. 2001.

Katz, "Waging War on Weeds", *Grape Grower*, vol. 27, No. 9, pp. 104, Sep. 1995.

"Marvin Stone's Personal Page", http://biosystems.okstate.edu/Home/mstone/INDEX.HTM, printed on Mar. 20, 2002.

McCabe, "Seeing the Light of Nitrogen", *Nebraska Farmer*, pp. 14-15, 20, Feb. 1996.

Moss, "Precision of Management of Turfgrass Using Optical Sensing", http://soil4213.okstate.edu/2003/moss_soil4213.ppt, pp. 1-14, 2003.

Newlin, "New Business, New Technology", http://www.stwnewspress.com/01/oct/16/sprayer.html, pp. 1-2, printed on Mar. 20, 2002.

Nitsch et al., "Visible and Near Infared Plant, Soil, and Crop Residue Reflectivity for Weed Sensor Design", *1999 International Summer Meeting sponsored by The American Society of Agricultural Engineers*, pp. 1-31, Jun. 1991.

NTech Industries, Inc., http://www.ntechindustries.com/ pp. 1, 2003.

"OSU Links Agreement with NTech; Nobel Laureate is Keynote Speaker", http://www.vpr.okstate.edu/research.NTECHpics.htm, pp. 1-3, printed on Mar. 20, 2002.

*Patchen: On Target*, pp. 1-4, Winter 1993.
*Patchen: On Target*, pp. 1-4, Spring 1994.
*Patchen: On Target*, pp. 1-4, Fall 1994.
*Patchen: On Target*, pp. 1-4, Spring 1995.

"Precision Agriculture, Oklahoma State University", "Soil 4213," http://soil4213.okstate.edu/index.html, pp. 1-4, 2002.

"Precision Sensing, Oklahoma State University", "Products", http://www.dasnr.okstate.edu/precision_ag, pp. 1-2, printed on Nov. 30, 2004.

*Prescription Farming™ Technology*, Soil Doctor Applications, Crop Doctor Applications, 12 pages, 1995.

Soil Doctor Systems, http://www.soildoctor.com/nindex.html, 1 page, 2001.

*Crop Technology, Inc.*, Price List, 2 pages, Jun. 1, 1995.

*The Best Kept Secret in Agriculture: The Soil Doctor Prescription Applicator*, Crop Technologies, Inc., 4 pages, Feb. 26, 1995.

*Soil Doctor Technology Accuracy*, Crop Technologies, Inc., 4 pages, Mar. 30, 1995.

"Reduced Herbicide Usage in Perennial Crops, Row Crops, Fallow Lane and Non-Agricultural Applications Using Optoelectronic Detection", *Patchen*, pp. 1-11, 1994.

"Robotics Institute: Automated Turf Management", http://www.ri.cmu.edu/projects/project_422.hmtl, pp. 1-2, printed on Nov. 30, 2004.

"Sensor Based Improvement on NUE: Can We Detect Nitrogen Deficiencies with Sensors?", http://www.dasnr.okstate.edu/nitrogen_use/sensor_based_improvement_of_nue.htm, pp. 1-7, printed on Mar. 20, 2002.

"Sensor Specifications", 1 page, Jul. 2004, Holland Scientific.

Shropshire et al., "Fourier and Hadamard Transforms for Detecting Weeds in Video Games", *1989 International Winter Meeting* sponsored by *The American Society of Agricultural Engineers*, pp. 1-18, Dec. 1989.

Shropshire et al., "Optical Reflectance Sensor for Detecting Plants", *Optics in Agriculture*, vol. 1379, pp. 222-235, 1990.

"Sucker Punch", *California Farmer*, pp. 18 and 20, Feb. 1995.

Notes from meeting with Bob Shearman of the University of Nebraska, May 9, 2001 (3 pages).

Script used by AllPoints during telephone screening for the first phase of Research study, Jan. 2003 (5 pages).

Script used by AllPoints during telephone screening for the second phase of Research study, Mar. 2003 (5 pages).

Moderator's Guide used by AllPoints for the first phase of Research study, Feb. 2003 (5 pages).

Moderator's Guide used by AllPoints for the second phase of Research study, Mar. 2003 (5 pages).

TMS Briefing Document shown to participants in the first phase of AllPoints Research study, Feb. 2003 (8 pages).

Email sent to participants in the second phase of AllPoints Research stuffy, Mar. 2003 (1 page).

TMS Briefing Document shown to participants in the first phase of AllPoints Research study, Mar. 2003 (7 pages).

\* cited by examiner

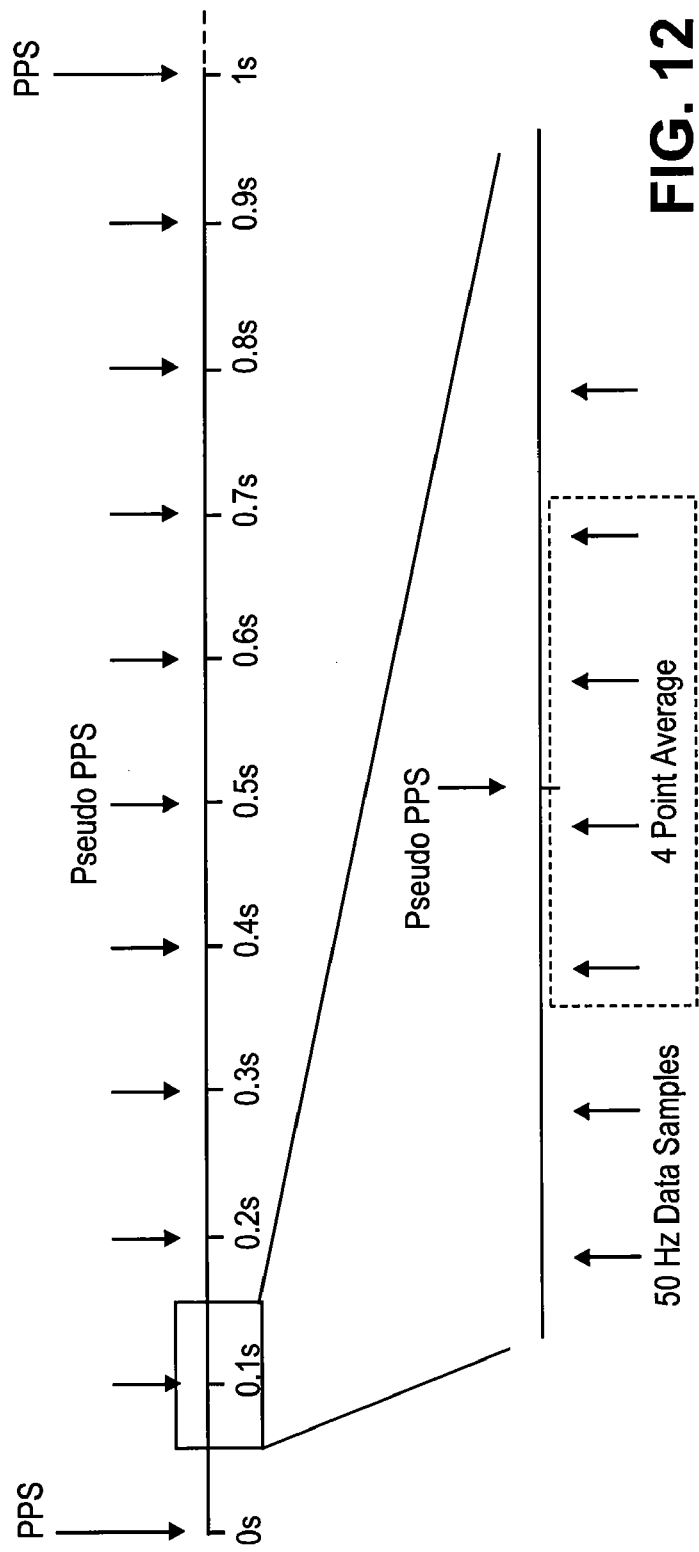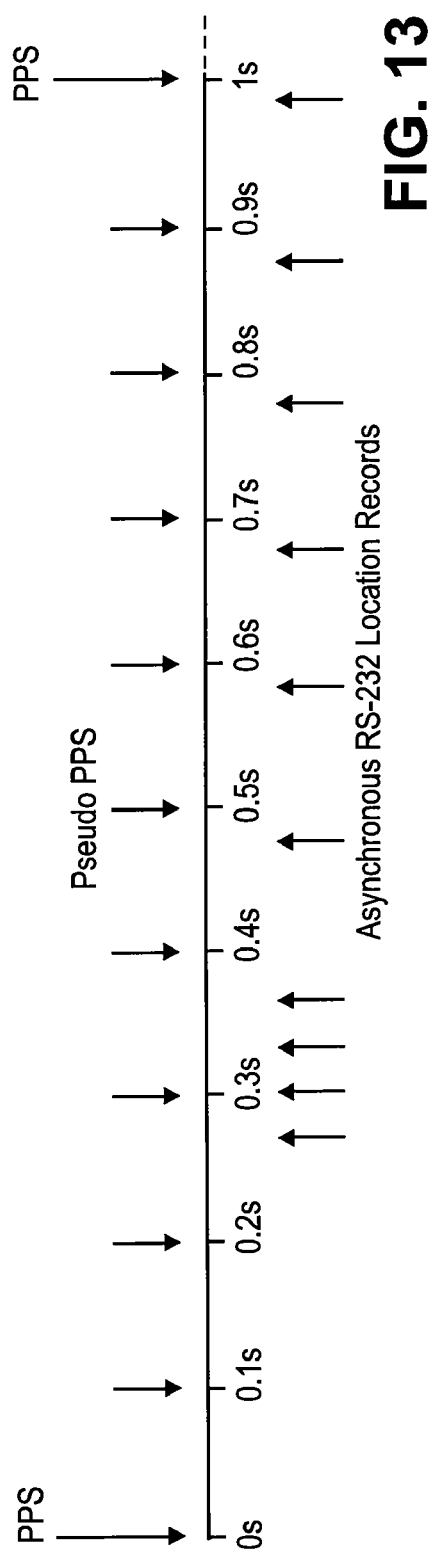
FIG. 12
FIG. 13

US 7,929,141 B2

SENSOR AND METHOD OF DETECTING THE CONDITION OF A TURF GRASS

RELATED APPLICATIONS

This application claims priority to US Patent Application Ser. No. 60/491,780, entitled SENSOR, filed on Aug. 1, 2003 by at least one inventor of the present invention, and to U.S. patent application Ser. No. 10/655,749, filed on Sep. 5, 2003, both of which applications are incorporated herein by reference.

FIELD OF THE INVENTION

The present invention relates generally to sensors, and in particular, to a sensor and method of detecting the condition of a turf grass.

BACKGROUND OF THE INVENTION

Turf grass, such as a part of landscaping or on a golf course, can often vary greatly over a given section. While some variations in the turf grass may be visible, other variations may not be obvious to an individual observing the turf, or may be in their early stages and will soon develop into significant variations. Further, some sections of turf grass may be extremely large, making it impractical for an individual to inspect all of the sections of the turf.

More importantly, many conventional devices currently employed to inspect a section of crops have a number of disadvantages. For example, many conventional devices use collimated illumination to detect the condition of crops. However, such illumination requires sensors which can be costly. Also, conventional devices employing the sensors are installed on equipment which do not provide uniform samples of the crop to analyze. For example, a sensor attached to a piece of farm equipment which does not provide an even vegetation condition will lead to results which are less reliable. That is, such conventional farm equipment does not provide consistent length or physical orientation of the crop, eliminate dew drops on the crop, reduce the effects of tire tracks, etc.

Accordingly, there is a need for an improved sensor for turf grass and method of detecting the condition of a turf grass.

SUMMARY OF THE INVENTION

A method of detecting the condition of a turf grass is described. According to one aspect of the invention, the method comprises steps of attaching a sensor to a mower; traversing a section of turf grass; and processing the output of the sensor.

According to another aspect of the invention, a method comprises steps of attaching a sensor to a mower; providing an illuminating pattern of light to the turf grass; and receiving a reflected pattern of light which is coincident with the illuminating pattern of light.

According to a further aspect of the invention, a method comprises steps of providing a plurality of illumination devices; coupling a feedback circuit to adjust the output of each illuminating device of the plurality of illuminating devices; detecting the irradiance of each illuminating device of the plurality of illuminating devices; and adjusting the irradiance of an illuminating device of the plurality of illuminating devices.

A method of detecting the condition of a turf grass according to a further embodiment comprises the steps of attaching a sensor to a mower; sensing the condition of the turf grass; and detecting the geographic position of the sensor while sensing the condition of the turf grass.

Finally, a method of detecting the condition of a turf grass according to a further embodiment comprises the steps of attaching a sensor to a mower; sensing the condition of the turf grass; detecting the geographic position of the sensor while sensing the condition of the turf grass; processing the sensor data and the geographic position data; and creating a map.

A device for detecting the condition of turf grass is also disclosed. The device comprises an array of illuminating devices generating a pattern of illuminating light; a detecting device receiving a pattern of reflected light which is coincident with the pattern of illuminating light; a detecting device adapted to detect stray light from the array of illuminating devices; and a feedback loop controlling the array of illuminating devices. A system employing the device is also disclosed.

BRIEF DESCRIPTION OF THE DRAWINGS

FIG. 12 is a timeline showing synchronizing data to pulses according to the present invention;

FIG. 13 is a timeline showing RS-232 events related to the sensor according to the present invention;

DETAILED DESCRIPTION OF THE DRAWINGS

Figure 1:
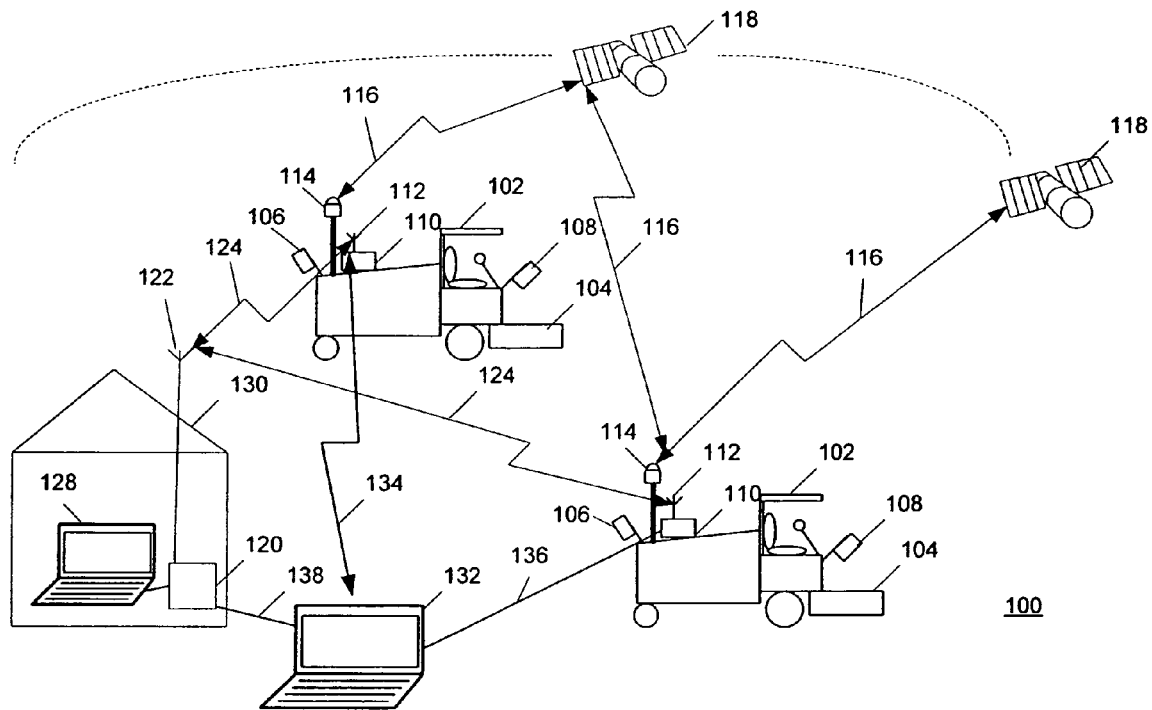
FIG. 1 is a system diagram of a system for detecting the condition of a turf grass according to the present invention.

FIG. 1 is a system diagram of a system for detecting the condition of a turf grass according to the present invention. In particular, a system 100 for detecting the condition of a turf grass comprises one or more mowers 102 having moving reels 104. One or more sensors 106 are attached to the rear of the mower, and one or more sensors 108 are optionally attached to the front of the mower. Although the sensors are shown attached to the front and rear of the mower, they could be attached to any part of the mower. Each mower also comprises a data logger 110 having an antenna 112 enabling the wireless transmission of data to a remote location, as will be described. The data logger also preferably comprises a global positioning system (GPS) antenna 114 for receiving position information of the data logger by way of a GPS communication link 116 with a GPS satellite 118. Alternatively, position information could be provided by any other suitable means, such as other satellite networks or triangulation in a cellular network, for example.

The system of the present invention also preferably provides automatic data transfer using wireless technology and a relational database with transaction support. Therefore, the system ensures data integrity and timely transfer of data. The sensed data detected by the sensors on the mower and GPS data received are coupled to a receiver 120 having an antenna 122 by way of a communication link 124. The receiver 120 could be coupled to or incorporated in a computer 128 in a base station 130. Such a base station could be in a garage or office of a golf course. Alternatively, the sensed data and GPS data could be coupled to a portable computer 132, such as a laptop computer using a wireless PC card, either directly by way of a wireless communication link 134 or by way of a wired communication link 136, or indirectly by a separate wired or wireless communication link 138.

Figure 2:
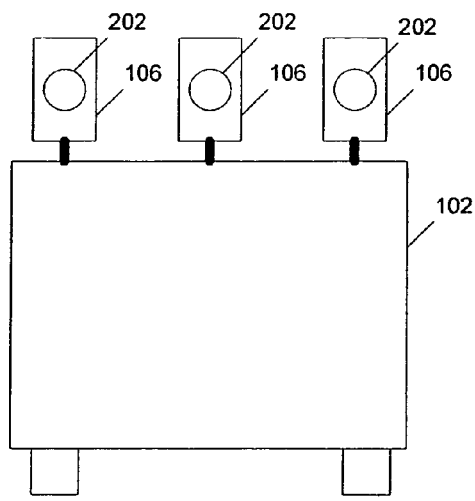
FIG. 2 is a rear view of a mower having a plurality of sensors according to the present invention.

FIG. 2 is a rear view of a mower having a plurality of sensors according to the present invention. In particular, three sensors 106 are shown on the back of the mower 102. Each of the sensors has an illumination window 202 for enabling the transmission of light incident to the turf and the detection of light from the turf. The sensor can be positioned at any horizontal or vertical angle as desired. The mounting could be a hinged mounting scheme that allows apparatus to be lowered out of the way before opening the mower hood. Alternatively, the mounting could be attached directly to the hood support so apparatus rotates with hood as hood opens. Both systems are preferably easily removed/attached between mowers of like kind.

Data from the turf sensor(s) 106 and 108 that is collected is preferably displayed using application software program that alerts the user to any new data sets that have become available since the last time the program was run. Such application software could be run on a processor of the data logger 110 in real time or otherwise, or could be run on a computer 128 or 132, or deferred. Once a data set is loaded into the application software, it can be viewed and manipulated any of a number of ways. The user can selectively filter data points based on the sensor ID, the state of the mower reels (active, inactive, etc), magnitude of the signal, time, or location. Time filtering is preferably employed for separating mowing events for a region in cases of multiple passes (e.g. double mowing). Further, a user specified transform can be applied to the filtered data, allowing after-the-fact calibration adjustment. A common use for this transform is "sensor balancing", whereby it is assumed that the mean value of all filtered data for a particular region is the same for all sensors, and each sensor's transform is adjusted accordingly.

Application software employed by the present invention preferably provides gridding of geographic data and automatically checks for new data on the base station. The sensed data could be processed and presented in a number of ways, including but not limited to trend maps, raw data, gridding of various sizes, standard deviation analysis, "removing-the-mean" analysis, displaying only data with reels active, displaying only data inside fairway outlines, data with sensor offsets automatically removed, etc. In displaying raw data, each measured data point is shown in the proper size and shape representing that sampled area and location on a 2D map using any of a number of color scales. Details of any specific point, including transformed values, time, location, etc. can be displayed. In displaying gridded data, data can be binned into any grid spacing, and displayed as a map of squares, using various color scales. Statistics for the data included in any target grid can also be displayed.

The system of the present invention provides numerous analytical tools for displaying the condition of a turf grass. One of the challenges in analyzing turf is the removal of the natural diurnal cycle of the turf response from longer term trends that are due to stresses of interest. The application software of the present invention achieves this by "mean removal", whereby the mean (or median) value for data in a particular region is computed and subtracted. A map of departures remains which, when color scaled appropriately, results in a map in which significant problem areas are readily visible.

Another challenge of the analysis of a turf grass is to highlight regions of otherwise healthy turf that have the beginnings of disease manifested by spots that are small in comparison to the area of one reading. The application software of the present invention achieves this by "MSD analysis", in which the product of the mean and standard deviation is computed for gridded data, and mapped. This analysis separates locations that are in the early stages of disease, where for example high mean equals healthy turf, and high standard deviation equals spots, from areas in which the problem is in the latter stages and more widespread (i.e. lower means and standard deviations).

A third analytical tool employed by the application software of the present invention is that of trend maps, in which rates of change of normal data (or mean-removed, or MSD) are displayed in a gridded map. The grid spacing and time domain are user selectable. The time history of the grid square in question can be displayed. As an aid to turf management, the application software also supports overlays containing other space and time based data, such as pictures, regions, and points, along with associated text. Additional analyses can be used to try to amplify, or otherwise bring out, areas in the turf that are of declining or poor quality. A few more specific examples of analyses that may be used are: standard deviation of the data points within a gridded area, a two dimensional spatial Discrete Fourier Transform (DFT) of the data points within a gridded area, a two dimensional spatial Fast Fourier Transform (FFT), or a variogram analysis.

Because dirt, grime or grass clippings on sensors and in the sensor's field of view (FOV) could impede the operation of the system, it may be beneficial to mount the sensors such that they are up and out of the debris field, and also provide a smaller mechanical profile to reduce likelihood of collisions. There are a number of advantages to putting the sensors behind the mower. Because the grass has just been cut and consistently oriented, the grass is of uniform length and physical orientation (i.e. bentness). The act of mowing also eliminates dew droplets on the grass, and reduces the effect of tire tracks. The rear placement also keeps the sensors out of the operator's typical working view. The design and operation of the sensor will be described in more detail in reference to later figures.

Figure 3:
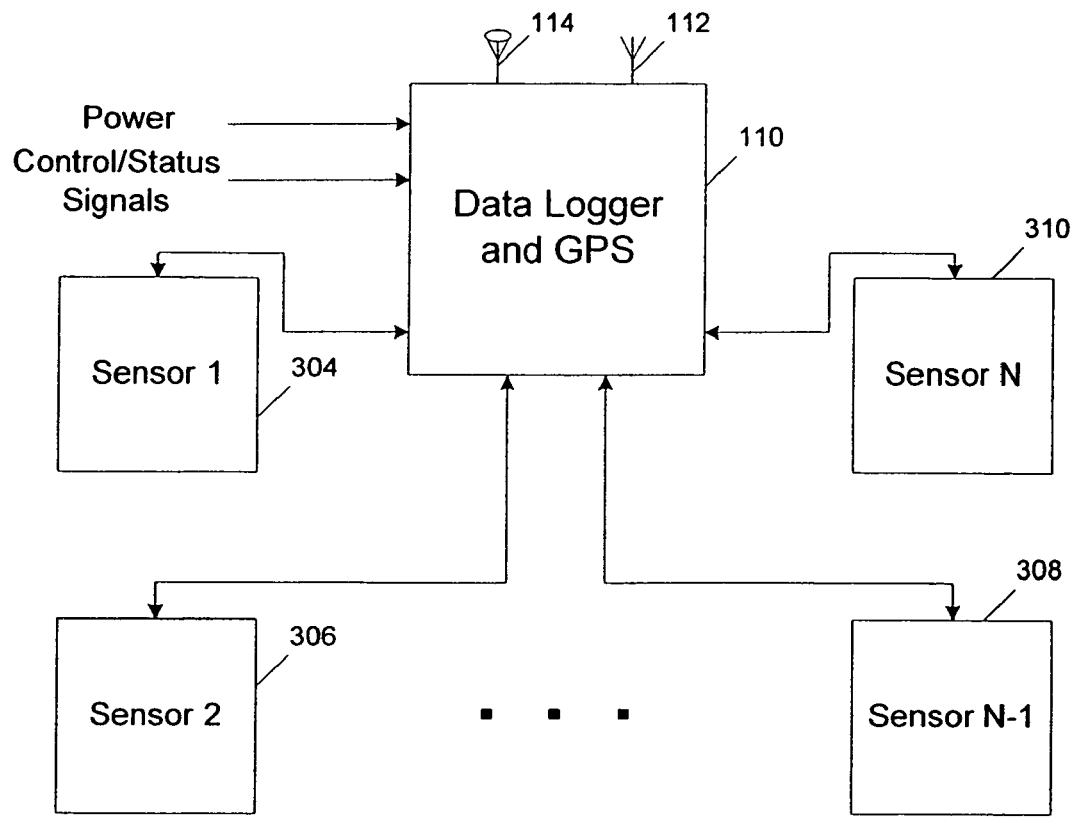
FIG. 3 is a block diagram of a mobile system according to the present invention.
Figure 4:
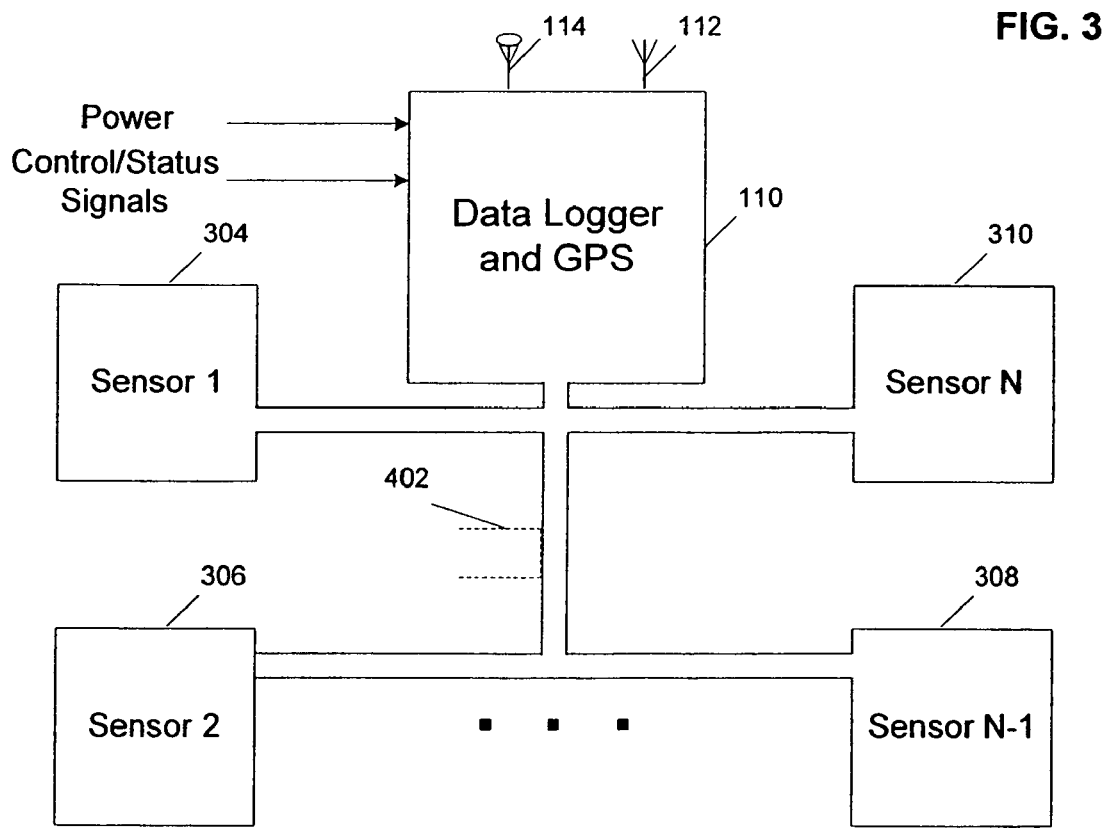
FIG. 4 is a mechanical diagram of the data logger and sensor according to the present invention.

FIGS. 3 and 4 are block diagrams which show the electrical and physical connections of the sensors to a data logger according to the present invention. In particular, power and control signals are coupled to the data logger 110, while electrical interface signals are transferred between the data logger 110 and the sensors 304-310. The block diagram of FIG. 4 shows a sealed system. Alternatively, because water penetration can occur during rapid cooling of the system, such as being washed with a garden hose, it may be beneficial to implement vented plumbing with or without filtered inlet, such as a vented system having a vent 402 shown in dashed lines. Such vented plumbing could be employed with or without filtered air inlet, intra-system vented plumbing, plumbing between components in the system, and/or use of GORE-TEX® venting. As will be described in more detail in reference to the block diagram of FIG. 5, the system of the present invention also preferably compensates for condensation by employing heated film with modulated power control or anti-fog coating.

Figure 5:
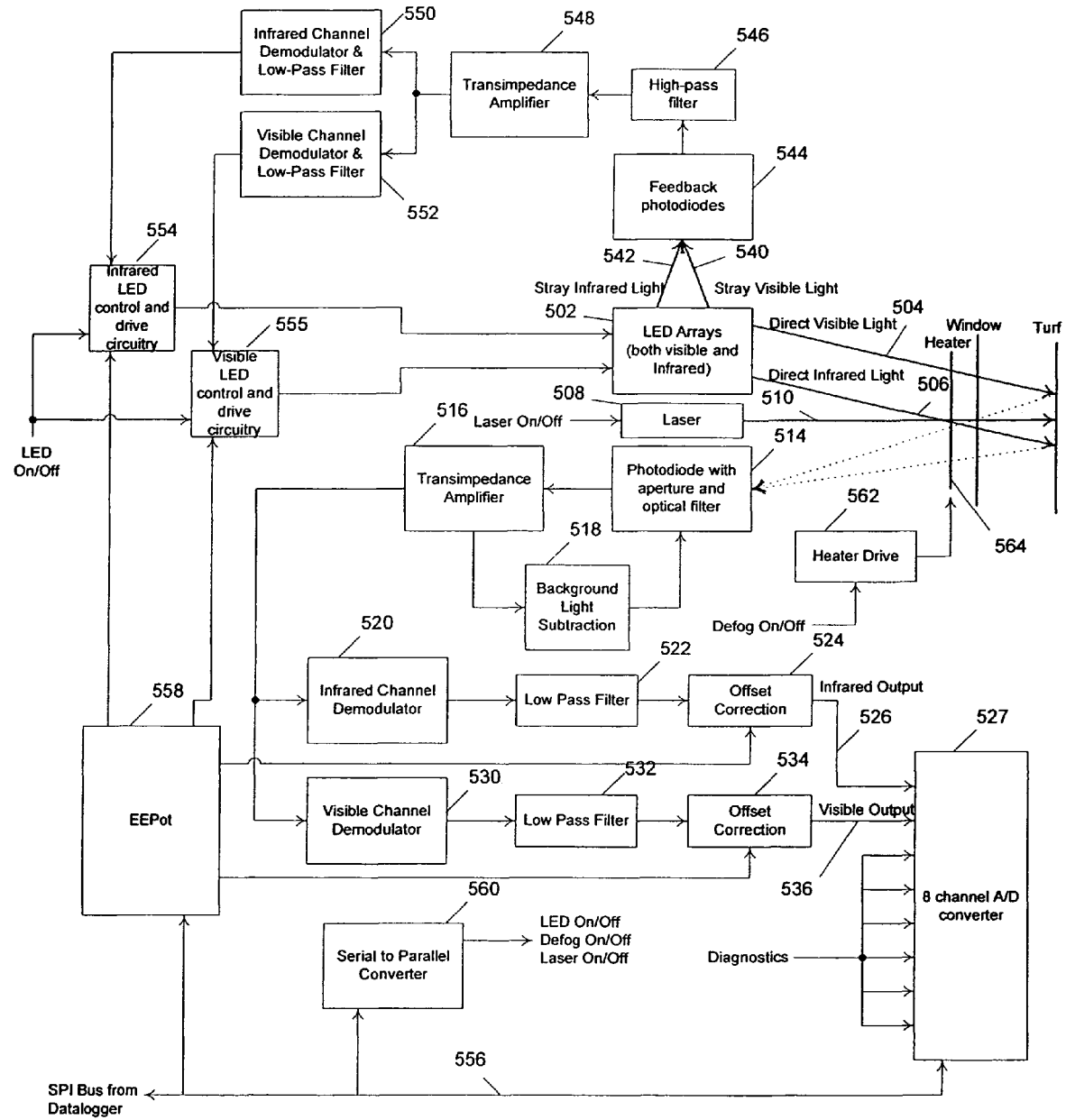
FIG. 5 is a block diagram of a sensor according to the present invention.

FIG. 5 is a block diagram of a sensor of FIG. 3 according to the present invention. In particular, an LED array 502 contains a plurality of LED devices, or some other illuminating devices. The array of LEDs preferably provide light of different wavelengths, such as a visible light beam 504 and infrared light beam 506. A laser 508 provides a laser light beam 510 to be used for aligning a calibration sample within the sensor's field-of-view. A photodiode 514 having an aperture and optical filter receives reflected light from the turf. An output of the photodiode 514 is coupled to a transimpedance amplifier 516. The transimpedance amplifier drives two separate paths. In particular, the first path comprises an IR channel demodulator 520 coupled to a low pass filter 522 and an offset correction circuit 524. The offset-corrected signal 526 is sampled by A/D converter 527. The second path comprises a visible channel demodulator 530 coupled to receive visible light and is coupled to a low pass filter 532 and an offset correction circuit 534. The offset-corrected signal 536 is sampled by A/D converter 527. Other types of illumination sources may be used, such as a filtered strobe lamp, etc.

The sensor also detects stray light from the LED array 502 in a feedback loop. In particular, stray visible light 540 and stray infrared light 542 are detected by feedback photodiodes 544. The orientation of the LED array and the feedback photodiodes will be described in more detail in reference to FIGS. 10 and 11. A high pass filter 546 receives an output of the feedback photodiodes and generates a signal to a transimpedance amplifier 548. The transimpedance amplifier 548 is coupled to an infrared channel demodulator 550 and a visible channel demodulator 552. The demodulator outputs are coupled to LED controllers 554 and 555. The A/D converter 527 is also coupled to an SPI bus 556 which controls an EEPOT 558, also coupled to LED controllers 554 and 555. As will be described in more detail below, LED controllers 554 and 555 control the output of the various LEDs to maintain constant LED output based upon signals detected by feedback photodiodes 544.

Figure 6:
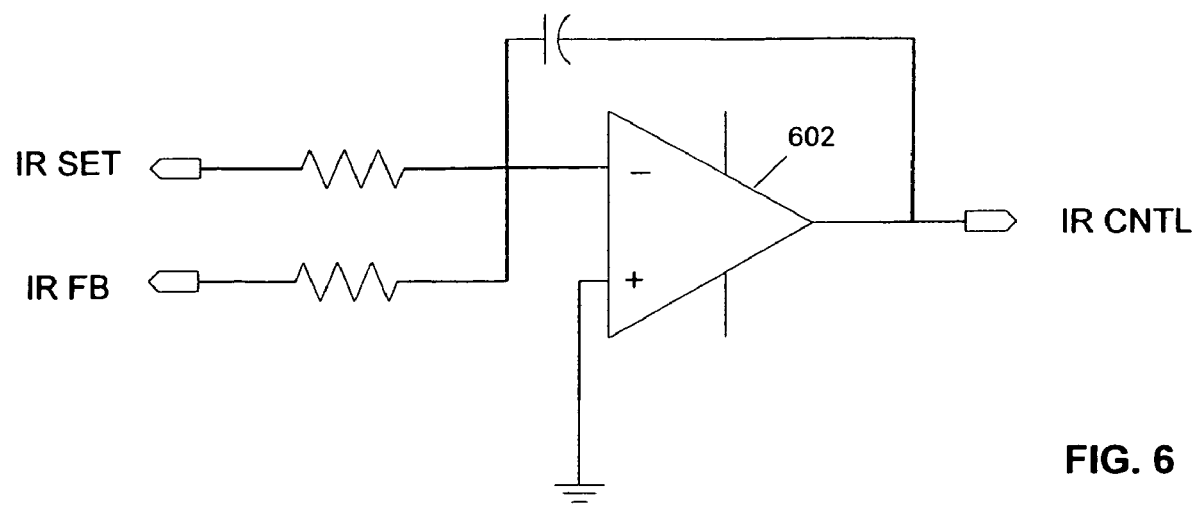
FIG. 6 is a circuit diagram of feedback and control circuit according to the present invention.

The system of the present invention provides constant LED output control by sensing stray illumination light via feedback photodiodes, which allows a repeatable, stable measurement of the reflected light. The output control circuitry is preferably implemented in hardware, including the feedback and control circuit of FIG. 6, and is therefore active in real time. Alternatively, output control could be performed by software.

Alternatively to measuring the stray light output with photodiodes or other photodetectors, other techniques could be used to measure and create a signal proportional to the light output, such as: directly sensing the amount of light that is directed at the target (e.g. positioning a photodiode such that it intercepts a portion of the illumination light); collecting stray light by use of a light pipe, or; sensing one or more electrical parameters, such as the electrical current that is driving the illuminating LEDs, which is proportional to the radiant intensity of the illumination LEDs. In the case of measuring the LED current, the temperature would also have to be known due to the LED's significant temperature dependence. By utilizing measurements of both the current and the temperature a very good representation of the light output could be calculated. Or by controlling both the current and the temperature, the light output could be controlled to a known radiant intensity. Finally, one of the parameters could be controlled while the other is just measured. This signal or value, obtained in any of the preceding ways, could be used to either control the illumination or be used to normalize the reflected light value.

By employing active illumination of two narrow band wavelengths, the system of the present invention is not dependent on sun/sky/daylight/shade conditions, and therefore can be operated anytime, day or night, by providing its own reference light source. The modulation/demodulation of the present invention allows ability to detect very small signals in the presence of large noise signals (i.e. sunlight, sun fleck, power source).

In addition to providing a means for separating the desired reflected light from other light sources (sun especially), modulation is also used to separate all the different simultaneous measurements. Within a single sensor, a number of different modulation frequencies are used, (for example, one for the infrared, and a second for the visible). The received signals are then demodulated at the correct corresponding frequency. This allows simultaneous measurements of all wavelengths of illumination. This is important to ensure that when calculating the desired output (e.g. IR/Visible), the measurement outputs are both representative of the same area of turf. If the measurements were made one after the other (e.g. time multiplexed), then the measurement outputs could be representative of different areas of turf. This is a source of error in the desired output.

Different modulation frequencies are also used between adjacent sensors. This is done to prevent optical crosstalk between sensors. For instance, if adjacent sensors were using the same frequency for the infrared modulation, then if one sensor's light output was partially illuminating the adjacent sensor's field-of-view, it would be a source of error. Therefore four different frequencies are used for modulation/demodulation within the system. Specifically, one for odd-numbered infrared, a second for odd-numbered visible, a third for even-numbered infrared, and a fourth for even-numbered visible. The sensors are always placed in numeric order so there is a pattern of odd-even-odd-even, etc. So crosstalk is possible from odd to odd sensor, but there is sufficient optical separation to prevent this. Testing has shown that if adjacent sensors are illuminating and viewing the exact same area there is no detectable crosstalk.

The data logger preferably is capable of detecting the type of sensor, including but not limited to detecting a model, a version of a sensor, technology type, a manufacturer, features of the sensor, etc. to enable the data logger to properly communicate with the sensor.

The system also preferably provides sensor on control and sensor off control by way of a serial to parallel converter 560. System on control could enable the system to turn on with key switch, with vibration of mower, by a manual switch local to the system which uses a diode to block the local "on" switch signal from "turning on" the rest of the mower. System off control preferably provides an off sequence beginning with key switch turning off. Data is transferred, if possible, or a software time out occurs, at which time the data logger and sensors turn off. Further, a hardware watchdog could be employed to turn off the system in event of a software failure. The watchdog is preferably activated when key switch is turned off, and then shuts off the system if a software controlled signal stops toggling for a predetermined number of seconds.

The key switch of the mower could also be employed to control the on/off state of the system of the present invention. In order to meet the user's needs, the system must be reliable and require a minimum of user intervention to operate. Ideally, from the user's point of view, the mower mounted portion of the system would be an extension of the host implement. The turn-off sequence is viewed as being more important than the turn-on event because a failure in the turn-off sequence has the potential for greater consequences to the user's equipment and work flow. An example would be a dead battery on the mower. This would cause significant annoyance and inconvenience for the typical user. Although a failure in the turn-on event would cause a lack of collected data, such a failure would not affect the performance of the main intention of the mower, that is, to mow the target turfgrass.

The key switch signal is detected by connecting a wire into the key switch wiring of the mower. This signal is then connected to the data logger of the system. Advantages of detecting the key switch include simplicity of implementation and straightforwardness of use. The data logger only turns on when the mower is in use and the data logger only begins its turn-off sequence when the mower is turned off. By only beginning the data logger turn-off sequence when the mower is turned off, an additional advantage is realized in that the mower will normally be turned off when the mower is in a known locale with respect to the base station-specifically, a locale in which wireless communications between the data logger and the base station can be achieved.

An example turn-off sequence would be as follows. When the turn-off sequence is initiated by the mower key being turned off, the data logger checks whether communication with the base station can be achieved, and also whether the data logger has any data to transfer to the base station. If communication is achieved, but no data is available for transfer, the data logger and sensors turn off relatively quickly (e.g. 2 or 3 seconds). If communication is possible and data is available to transfer, the data is transferred. At the completion of the data transfer, the data logger and sensors turn off. If communication is not established, a software timeout is implemented in the data logger to limit how long the data logger attempts to connect to the base station. At the end of this timeout period, (e.g. a few seconds to a few minutes, although any appropriate time period could be used), the data logger and sensors turn off. Data still resident on the data logger is maintained until it is transferred to the base station.

Various other means could be employed to provide the information about whether to turn on or off the data logger. For example, vibration from the implement, heat from the exhaust manifold or pipe, or electrical impulses in the spark plug wires or other electrical device on the mower could be detected. Detecting vibration would allow the mower mounted portion of the system to be more autonomous, that is, less dependent on inputs from the mower for its operation. The vibration detection circuit could be mounted inside the data logger, making connection of the system to the mower more simple. Similarly, as the exhaust pipe of the typical mower exists from the rear of the mower, attachment of a sensor to the exhaust pipe could entail less wiring than to the key switch.

Because the system of the present invention could collect data from the sensors whenever the mower is moving and the GPS is providing differentially corrected position information, a method is needed to discriminate between when the turf grass is being sampled under consistent, "known" conditions and when it is not. For example, the system could collect data on a golf course as the mower is driving from the shed to the target fairway, over other fairways to reach the target fairway, is turning around in the rough of the course, etc. According to one embodiment of the invention, an electrical signal exists on the mower that indicates when the reels are in mowing position and the reels are actually mowing. For purposes of this document, this signal is called the "reels active" signal. A reels active signal, which senses when mowing is in progress, could provide a simple method of determining when data is being collected under the appropriate conditions to allow sorting of data between valid data and invalid data. Such a signal also enables a method of including/eliminating collected data offset in distance or time from the actual signal change. For example, if the sensors are viewing an area behind a forward-moving mower, when the reels are raised the sensors have not yet viewed the total mowed area. Likewise, at the instant when the reels are lowered, the sensors are not viewing mowed turf They will view the mowed turf some traversed distance later. So collected data marked as valid may be offset in time or distance to minimize this effect. The offset could be performed in either direction depending on the location of the sensors.

This signal exists on the mowers in the form of a reels solenoid signal. It is typically active (i.e. carrying an electrical signal of approximately 12V D.C) when the reels are in mowing position and the "mow" switch is engaged by the user. The "reels active" signal is typically inactive (i.e. carrying an electrical signal of approximately 0V DC) when the reels are not in the mowing position OR the "mow" switch is not engaged by the user. Use of this "reels active" signal allows the system to determine when the sampling of the turf grass was performed while the turf grass was in a known condition. Without this, the conditions of the turf grass during sampling is not known, which introduces additional ambiguities into the analysis results. The known conditions of the turf grass provided by the "reels active" signal include, but are not limited to: a consistent turf grass length over the entire fairway; the dew droplets having been removed from the turf grass blades; the turf grass has been rolled, or mechanically positioned, by the mower such that the effect of the mower tire tracks is significantly reduced, etc. To implement detection of this signal, electrical wiring is installed on the mower and connected to any of the "reels active" signals, (i.e. the front, rear, or any other "reels active" type signal), and this wiring is routed to the data logger where the state of this "reels active" signal is logged with the sampled data.

Figure 7:
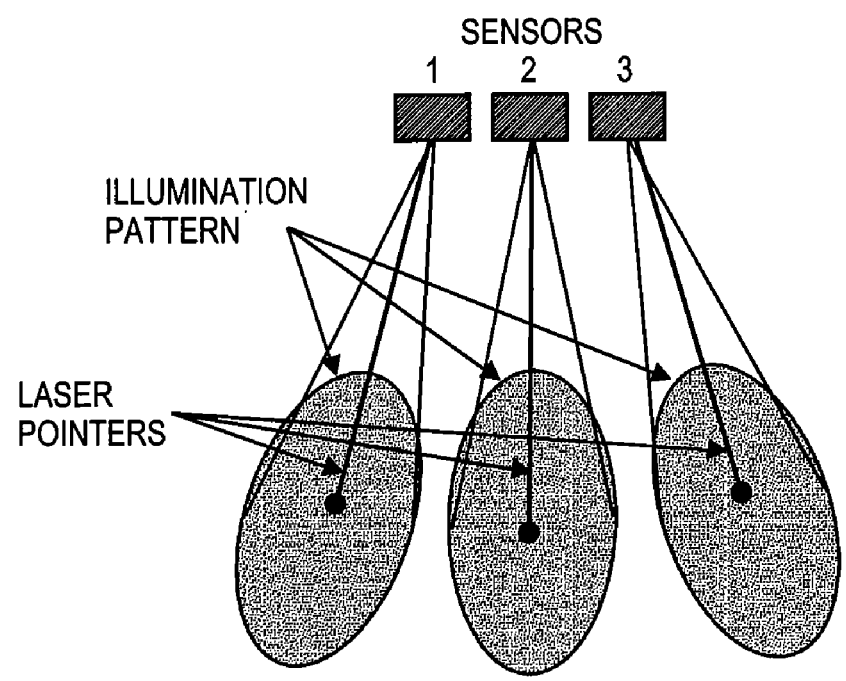
FIG. 7 is an elevational view showing the operation of turf sensors according to the present invention.
Figure 8:
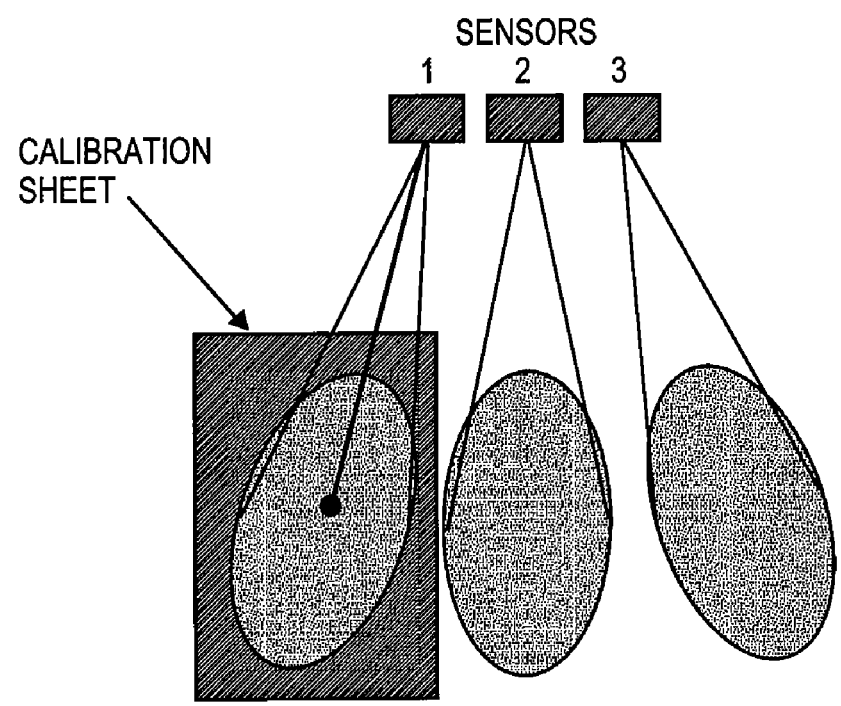
FIG. 8 is an elevational view showing the calibration of a turf sensor according to the present invention.

FIGS. 7 and 8 are elevational views showing the operation of turf sensors according to the present invention. In particular, the illumination pattern of the sensors along with the laser pointers, which are used in the calibration procedure to show the mower operator where to place the calibration sheet, are shown. The laser pointers also indicate when to move the calibration sheet to the next sensor and when the calibration procedure is finished.

As shown in FIG. 8, a calibration procedure is used to normalize sensor values between each sensor. A standard calibration sheet is placed in the field of view of each sensor to calculate multipliers for the IR and visible channels on each sensor. A calibration button is used to start the calibration procedure, and to progress from sensor to sensor. A handheld computer can be used instead of the calibrate button and to control the calibration and monitor the result. This procedure preferably uses 3 sensors, although any number of sensors could be used. At the end of the calibration, the new calibration multipliers and some diagnostic values are saved in a log entry. When the mower operator initiates the calibration by pressing the calibrate button, the current calibration multipliers are saved in case the procedure is aborted. The procedure can be aborted at any point by holding the calibrate button in for more than 2 seconds. The saved calibration multipliers are then restored for use. During the calibration, a sensor can be skipped by pressing the calibrate button 2 times. The saved calibration multiplier is then used for that sensor and all other sensors are calibrated normally.

Figure 9:
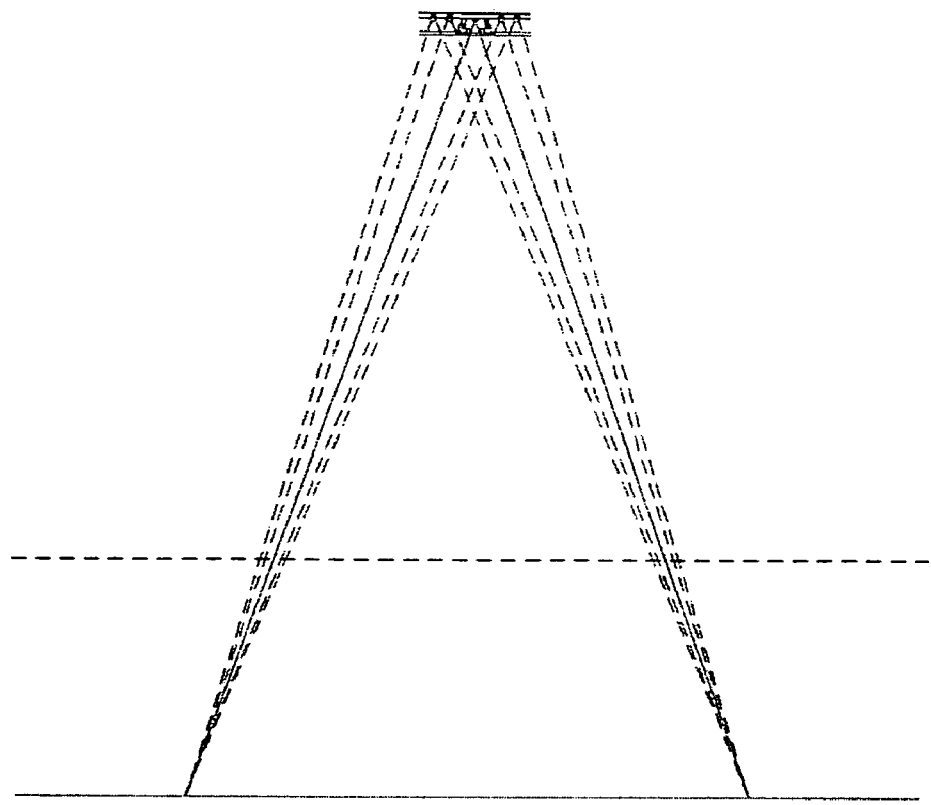
FIG. 9 is a cross-sectional diagram showing the projection and reflection of light according to the present invention.

FIG. 9 is a cross-sectional diagram showing the projection and reflection of light according to the present invention. In an optical system such as the one described in this invention, it is often desired to have the measurement results independent from the measurement distance. This is difficult because the signal is reduced by the square of the distance from the sensor to the sample. If the desired output is a linear ratiometric formula of two signals, and if the signals both vary by the same proportional amount versus distance, then the output will remain constant.

The present invention provides a novel method of providing such an output without using any lenses, mirrors, or other focusing or collecting devices. Unlike prior art methods which often use collimated illumination and detection arrangements to achieve the above described goals, the system of the present invention uses coincident patterns of light.

In particular, as shown in FIG. 9, a sensor with an array of light source is used to illuminate the sample. In the middle of the illumination array is the detector. The detector collects the reflected light from the sample. In the drawing the solid lines represent the detector's field-of-view (FOV) and the dashed lines represent the output light from the LEDs that is within the detector's FOV. There may be light outside of the FOV, but it is not shown in this example. Normally this arrangement is used at some oblique angle with respect to the sample (as shown in FIG. 1) so any specular component of the reflection is reflected away from the detector. Only some small fraction of the reflected light will actually make it back to the detector. Only the light that is illuminating the detector's field of view can have an effect on the output. Illumination light that falls outside the field of view is rejected by an aperture located in front of the detector. Notice that with just an aperture limiting the collected light, it is a focus-free detection system. There is no focal length, and no such thing as being out of focus. There is some small amount of blurring at the edges of the field of view due to the finite size of the detector. The radius r of the aperture along with the distance d from the detector determines the angle θ of the field of view [θ=tan$^{-1}$(r/d)]. Because it is normally a non-0° angle (non-collimated), as the distance varies the viewed area will change. However, if the aperture angle is small, then the viewed area does not change quickly with distance. For many applications, the size of the viewed area is not a critical parameter.

The same illumination/detection pattern with the viewed sample at a closer distance, represented by the dashed horizontal line, is shown in FIG. 9. The dashed lines show that the illumination no longer intersects the FOV at the sample. This shows a small error in the illumination versus detection area. Fortunately, as a percentage of the area, the error is small. Also, the radiant intensity of the source is usually not constant versus output angle. It is normally reduced at the edge of the FOV as compared with the middle. Therefore the total radiant power does not decrease as quickly as the decrease in area. This fact also minimizes the effect of the error.

Actual test results can confirm how well this arrangement works. For a distributed circular array 3.25" in diameter, with a 12° half angle FOV aperture in front of the detector, the distance error in the ratio is less than 0.1% per 6" change over a range from 42 to 60 inches. The error gets worse as the sample gets closer. For example, there is a 0.6% error in going from 36 to 42 inches. This worsening effect is evident by looking at FIG. 9. The fact that the illumination array has some finite distribution is more significant at close distances.

It should be clear that as the distributed source is reduced in size the error is reduced. It is therefore advantageous to design the illumination array to be as small as possible and located as close as possible to the detector. If the source could be reduced to a point and located at the exact same location as the detector, the illumination and detector FOV would be perfectly coincident resulting in no error in the ratiometric output as the distance is varied. Because this is not practical, it is the most advantageous to make the ratio of viewing distance to array size as large as possible, while taking the disadvantage of distance into account.

Figure 10:
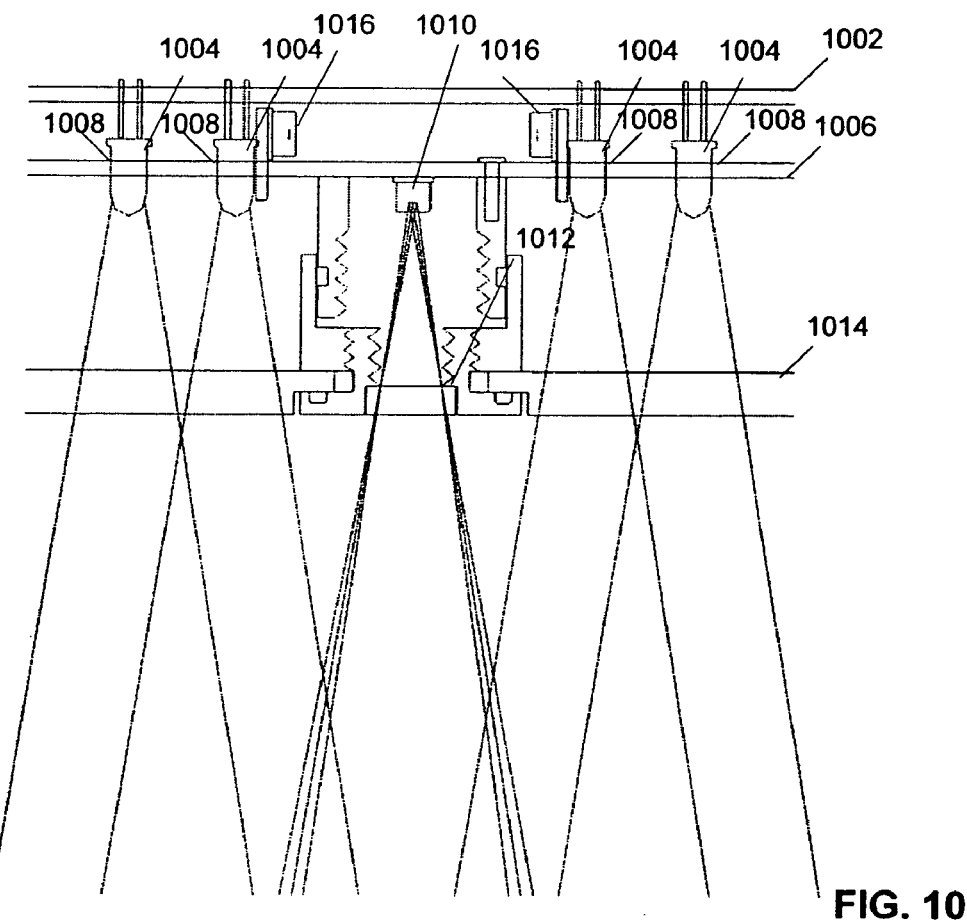
FIG. 10 is an enlarged cross-sectional diagram showing the projection and reflection of light according to the present invention.

FIG. 10 is an enlarged cross-sectional diagram showing the projection and reflection of light according to the present invention. In particular, a first circuit board 1002 having a plurality of LEDs 1004 is coupled to a second circuit board 1006 having a plurality of holes 1008 for receiving the LEDs 1004 and providing mechanical support for the LEDs. The second circuit board, which could be a printed circuit board having components for the sensor, also provides a means for directing the stray illumination light to the feedback photodiodes while blocking the majority of the undesirable reflected illumination light, and provides electrical separation between the modulation and demodulation circuits. A photodiode 1010 receives reflected light through an aperture 1012 from light transmitted through a window 1014. A pair of photodiodes 1016 is used to sample a representative portion of the illumination light. The output of these photodiodes is used within the closed-loop feedback system described in FIG. 5 to maintain the LED output at a constant power. The two circuit boards provide the electronics for the sensor, and enable a design that wraps many necessary and desired features into a very compact and multi-purpose packaging arrangement.

As can be seen in FIG. 10, the optical arrangement of the present invention provides a cone of illumination light which is coincident with the cone of received, reflected light. It also provides large rejection of height variation for linearly ratioed sensor outputs. The aperture is provided through the illumination window to prevent undesired illumination light from reaching the receiver and also creates an environmental seal with the illumination window. Light is blocked that would reflect off the board or that would bounce inside the window material and otherwise would dump into the receiver. Other coincident geometric patterns of illuminated and received light may be used; the cone geometry is only one example.

In addition to mechanical support, the arrangement shown here also provides electrical separation between the illumination and detection sections of the sensor. This arrangement also provides proper light blocking and containment features. Since the second circuit board 1006 is mostly solid except for the LED holes, it blocks most of the reflected light signal from reaching the feedback photodiodes 1016. The arrangement of the circuit boards also keeps most of the stray light from the LEDs contained so it can be received by the feedback photodiodes. Without the light blocking feature, the reflectance of the sample could affect the output illumination by adding a small amount of light proportional to the sample reflectance to the direct stray light that is intended on being collected by the feedback photodiodes.

Figure 11:
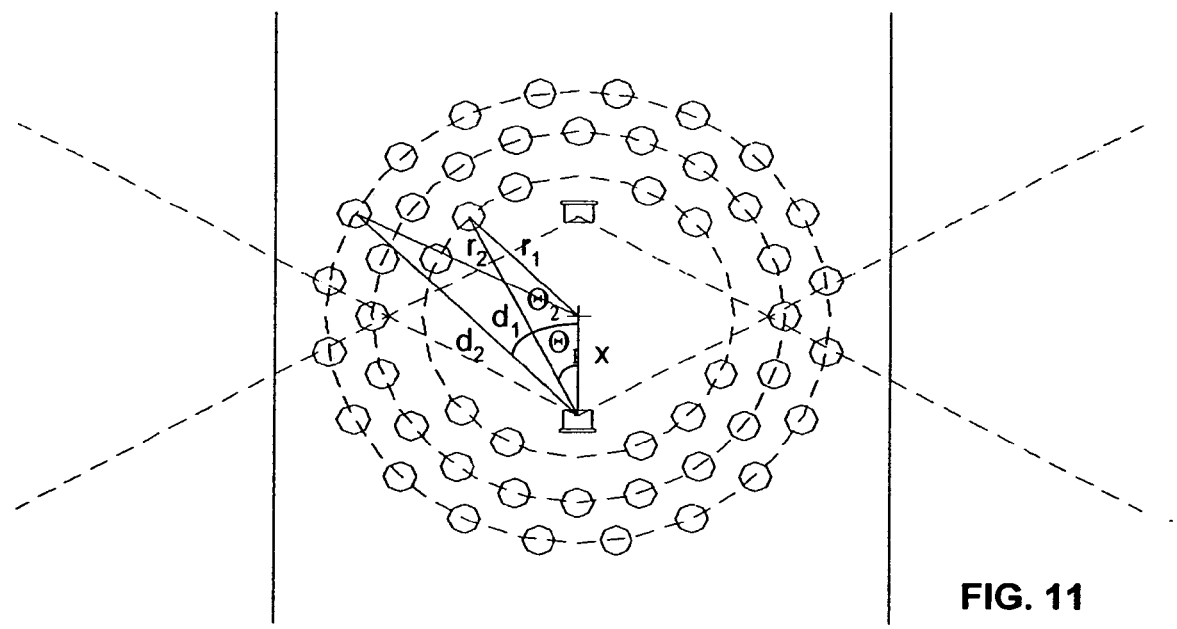
FIG. 11 is a top plan view showing the light emitting diodes (LEDs) and feedback photodiodes according to the present invention.

FIG. 11 is a top plan view showing the light emitting diodes and feedback photodiodes according to the present invention. The system of the present invention also provides "even" weighting of the illumination LEDs' output light into the feedback photodiodes, due to geometrical position of the illumination LEDs and the angular response of the feedback photodiodes. According to the present invention, a circular array of LEDs is used for illumination of the sample. The output of the LEDs is very temperature dependent. The output can also vary over time from aging effects. Because it is beneficial that the irradiance stays constant, a feedback system is used to maintain the irradiance at a constant level. Some optical arrangement is required to collect a representative portion of the output light, measure its intensity, and appropriately adjust the drive circuitry to hold the irradiance constant. Since all the LEDs are used for illumination, it is desired that all also contribute to the proportional feedback signal. An equal contribution from each LED in the array is desired, regardless of its position in the array. This will ensure that if any single LED is varying by a different amount than the others, the feedback circuit will adjust the total output accordingly.

By careful placement of the detectors used for feedback within the array of LEDs, offsetting optical effects are used to help even out the feedback contribution from each LED in the array. As a source emits light its irradiance falls off with the square of the distance (i.e. $E_e \propto 1/d^2$). Therefore LEDs close to the detector have a larger irradiance than those further away. The present invention shows a technique to minimize this undesired effect. Because of this particular arrangement, the LEDs that are close to the detector are also at a significant angle with respect to the normal angle of the detector. A standard photodiode detector has an angular sensitivity proportional to the cosine of the incident angle (i.e. $S \propto \cos(\theta)$). So the partial output from the detector is the product of the incident irradiance from a particular source and the sensitivity of the detector to a source from that particular angle (i.e. $O_i \propto \cos(\theta_i)/d_i^2$). The total output of the detector is proportional to the sum of all the sources in the field of view (i.e. $O \propto O_1 + O_2 + \ldots + O_n$). Only the LEDs within the detector's field of view contribute to its output.

The distance d shown in FIG. 11 is calculated as follows:

$$d_i = x \cdot \cos(\theta_i) + \sqrt{x^2 \cdot \cos^2(\theta_i) - x^2 + r_i^2}$$

where r is the radius of the circular array, and x is the distance from the center of the array to the detector.

Substituting into the above equations gives the following for the partial output formula:

$$O_i \propto \frac{\cos(\theta_i)}{\left[ x \cdot \cos(\theta_i) + \sqrt{x^2 \cdot \cos^2(\theta_i) - x^2 + r_i^2} \right]^2}$$

and the total output formula is:

$$O \propto \sum_{i=1}^{n} \frac{\cos(\theta_i)}{\left[ x \cdot \cos(\theta_i) + \sqrt{x^2 \cdot \cos^2(\theta_i) - x^2 + r_i^2} \right]^2}$$

Figure 21:
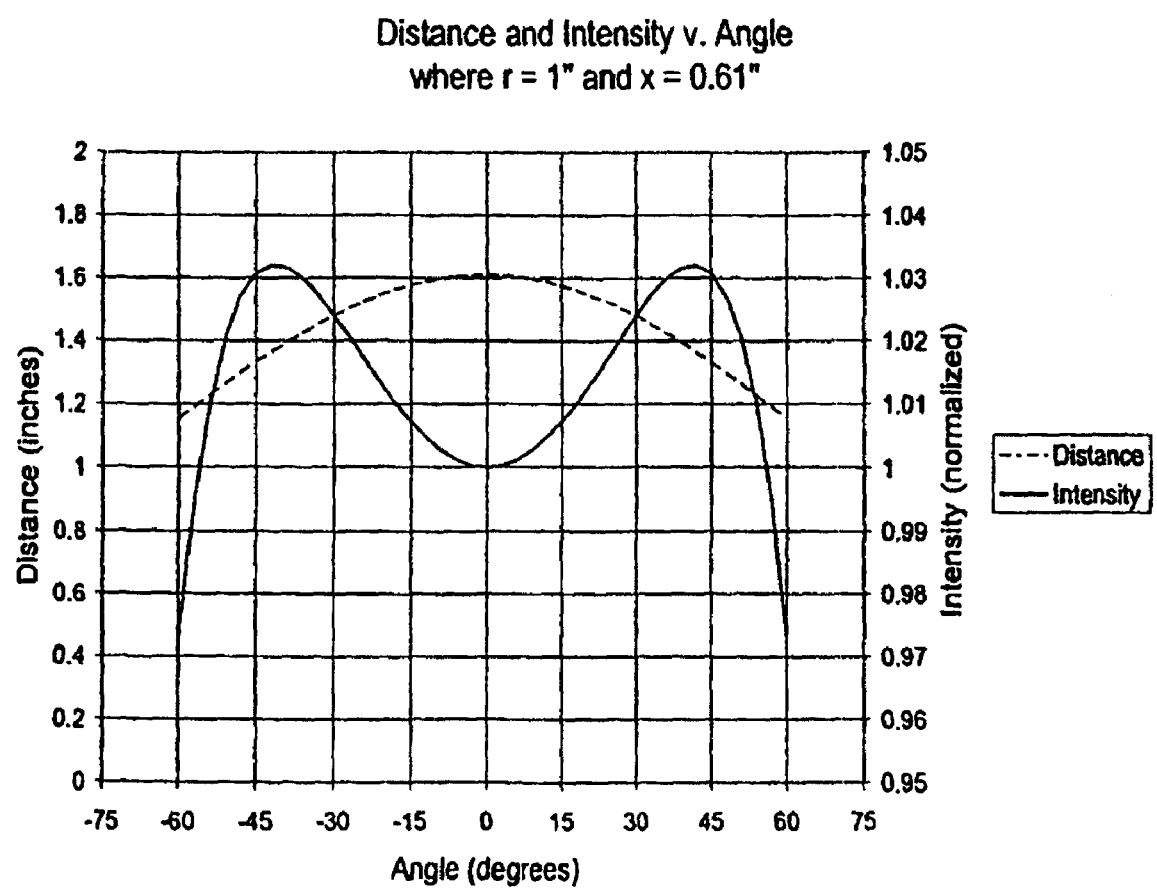
FIG. 21 shows a plot of distance and normalized intensity.

In the case of a single circular array (all at one radius) of LEDs, a very good equalization can be done by proper placement of the detectors with respect to the LEDs. For instance with r=1", and x=0.61" and including all LEDs within a 120° total field of view, the maximum partial output in normalized units is 1.032, which occurs at 42°. The minimum partial output is 0.973 at 60°. This is only a difference of −5.7%. The standard deviation of 5 sources evenly spaced from 0 to 60° is only 0.78%. A plot of the distance and normalized intensity is shown in FIG. 21.

When multiple circular arrays are used at several different radii, the technique is not as successful, but yet still yields favorable results. For instance, with $r_1$=0.97", $r_2$=1.26", and $r_3$=1.55", and x=0.64", the overall maximum point to point weighting difference is −61%. This is from row 1 at 48° to row 3 at 60°. Within a single row, the results are more favorable. Maximum weighting differences are: row 1=−6.5%, row 2=−14%, and row 3=−23%. Therefore if the weighting between rows is not important, the differences are small. For instance, if each row contains a different color LED, and each color is controlled independently, then equal weighting between rows is not important.

By using two or more detectors, the outputs can be combined to view most or all of the LEDs in the array. As shown in the embodiment of FIG. 11, only 2 out of 50 LEDs will not have much effect on the feedback circuit. The missed LEDs are hidden behind the opposite detector. Accordingly, those LEDs could be either moved into the field of view or removed from the array if their effect on the feedback circuit was deemed important.

While the benefits of a circular array have been addressed here, other configurations could also be used. A linear array may be desired to minimize the overlap of successive samples of the sensor. Other shapes or techniques may also be used. Although the even-weighting advantages of the circular arrangement were discussed, the benefits of other arrangements may be deemed more important than the precision of the light output.

Various technologies are used to make reports available in a convenient and timely fashion. Refering to FIG. 1, raw data is transferred automatically from the mower 102 to the base station 128/130 using wireless networking 124 and a webserver. The base station 128/130 processes the data and posts it into a relational database. The raw data is compressed in order to optimize the data transfer 124. The relational database contains geographical support for efficiently handling location data greatly reducing the time needed to generate a report.

FIG. 12 is a timeline showing synchronizing data to pulses according to the present invention. The method of aligning sensed data with position data according to the present invention could employ a number of techniques, including using pulse-per-second output from position determining unit, oversampling sensed data, and using a custom synchronization algorithm to align the oversampled sensed data with the position data.

The positioning system outputs an electronic Pulse Per Second (PPS) that indicates the precise time when a location measurement occurs. The PPS triggers an interrupt to inform the software of the event. By definition, the PPS occurs once at the beginning of every second even though the positioning system outputs location records 10 times per second. In order to synchronize the sensor data with the location records, the software preferably generates 9 pseudo PPS pulses for every 1 PPS as shown in FIG. 12. The PPS and pseudo PPS pulses are used to synchronize the 50 Hz sensor data streams, for example, to the 10 Hz location records. The software collects data samples from the sensors at 50 Hz, for example. After a PPS (or pseudo PPS) occurs, 2 more data points are collected and averaged with 2 data points from before the PPS. This gives a sensor value that is the average of 4 samples and centered in time on the PPS. The location records are sent over an RS-232 line some time after the PPS. Even though the Positioning System outputs location records at 10 Hz, the records are not output at fixed time intervals.

Figure 14:
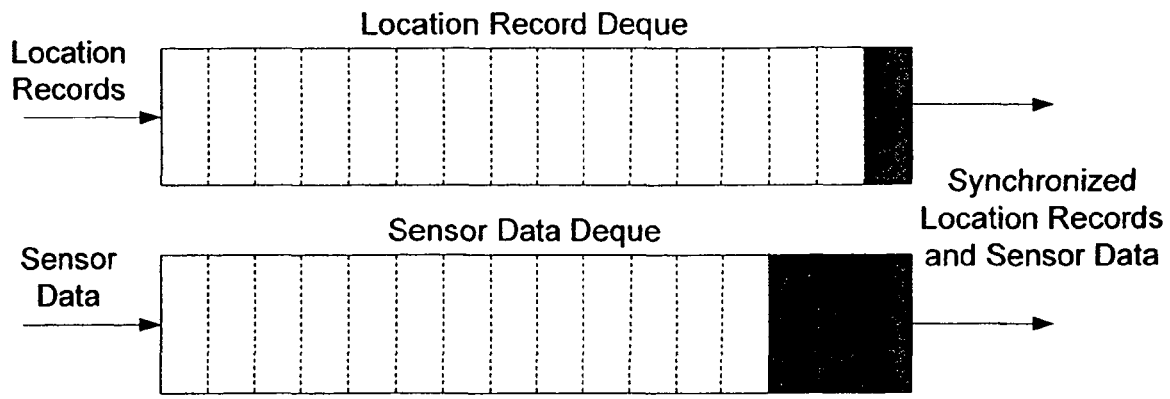
FIG. 14 is a diagram showing synchronizing location records and sensor data according to the present invention.

FIG. 13 is a timeline showing RS-232 events related to the sensor according to the present invention. FIG. 13 illustrates the variable delay between the PPS and the time when the location record is output. The software must compensate for this feature by collecting and holding onto one or more sensor data values until the location record corresponding to that data is received. A Double Ended Queue (deque) for the sensor data and another deque for the location records are used to perform this synchronization as shown in FIG. 14. Location records and sensor data are inserted asynchronously into the left end of the deques and synchronized location and data are pulled from the right end of the deques. This allows the software to collect and hold multiple data for each sensor until the appropriate location record is received. Then both the location record and sensor data are stored in a data file.

Figure 15:
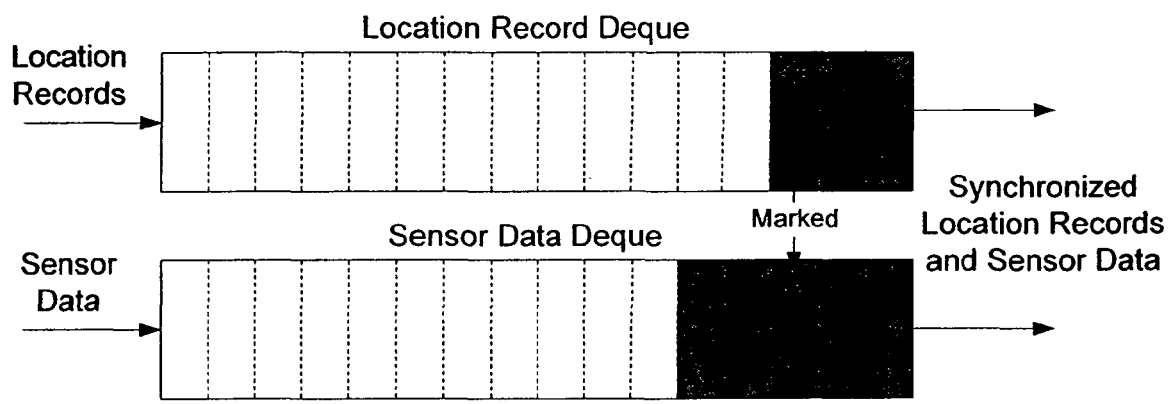
FIG. 15 is a diagram showing synchronizing location records and sensor data marked with pulse per second according to the present invention.
Figure 16:
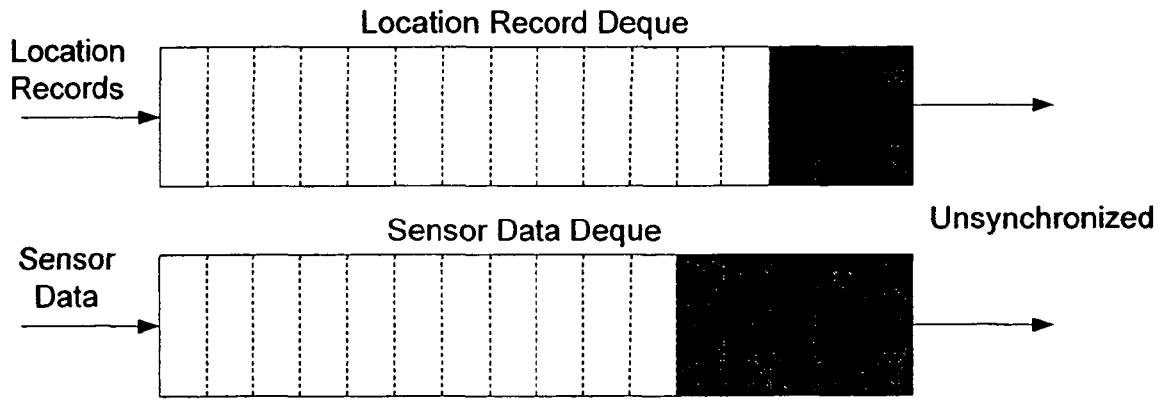
FIG. 16 is a diagram showing deques that are unsynchronized according to the present invention.

Each sensor data point and each location record is also marked as to whether it was collected coincident with a PPS as shown in FIG. 15. Sensor data and location records collected because of a pseudo PPS are not marked. This allows the deques to be synchronized to each other as shown in FIG. 15. Marked sensor data and marked location records should be pulled off the right end of the deques at the same time. If a location record at the right end of the deque is marked and the data sensor data is not, then the deques are not synchronized as shown in FIG. 16.

The following method is preferably used to get the location deque and sensor data deque synchronized. All sensor data and location records are discarded for 1 second. This flushes all data out of the deques and from the buffers in the RS-232 link. All sensor data and location records are discarded until a marked location record is received. All sensor data and location records are then discarded until 3 location records have been discarded. This is to ensure that the next few location records and sensor data will be between PPS pulses. All unmarked sensor data and unmarked location records are discarded. When the next marked sensor data or marked location record is received, they are pushed into the left side of the deques. The right end of the deques are now synchronized. If the deques ever become unsynchronized as shown in FIG. 16, the procedure is repeated to re-synchronize them.

Figure 17:
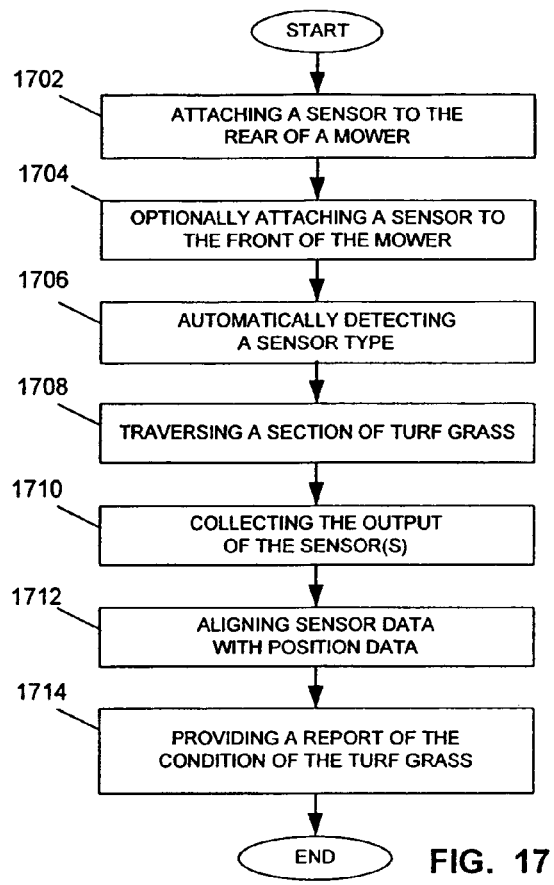
FIG. 17 is a flow chart showing a method of detecting the condition of a turf grass according to the present invention.

FIG. 17 is a flow chart showing a method of detecting the condition of a turf grass according to the present invention. In particular, a sensor is attached to the rear of a mower at a step 1702. A sensor is optionally attached to the front of the mower at a step 1704. The sensor type may be automatically detected at a step 1706. A section of turfgrass is tranversed by the mower at a step 1708. The output of the sensor(s) is collected at a step 1710. The sensor data is aligned with position data at a step 1712. Finally, a report of the condition of the turfgrass is provided at a step 1714.

Figure 18:
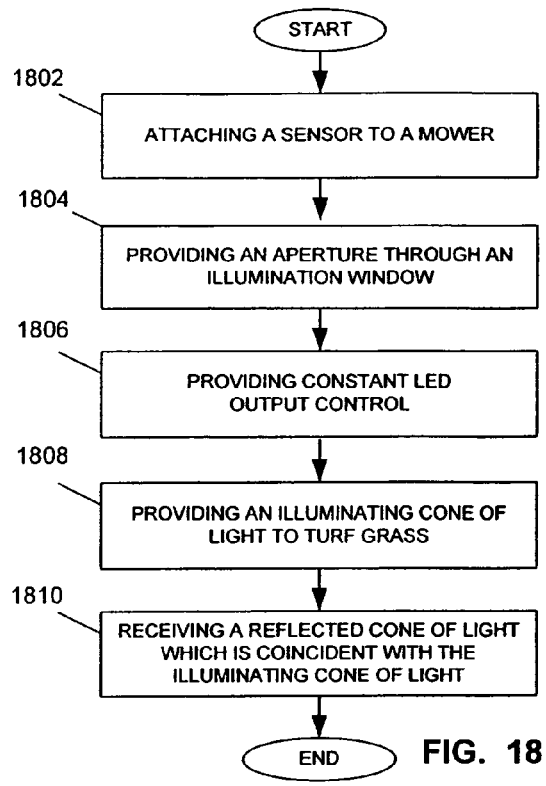
FIG. 18 is a flow chart showing a method of detecting the condition of a turf grass by providing incident and detected light which are coincident according to an alternate embodiment of the present invention.

FIG. 18 is a flow chart showing a method of detecting the condition of a turf grass by providing incident and detected light which are coincident according to an alternate embodiment of the present invention. In particular, a sensor is attached to a mower at a step 1802. An aperture is provided through an illumination window at a step 1804. A constant LED output control is provided for a plurality of LEDs at a step 1806. An illuminating light is provided to a section of turfgrass at a step 1808. Finally, reflecting light which is coincident with the illuminating light is received at a step 1810.

Figure 19:
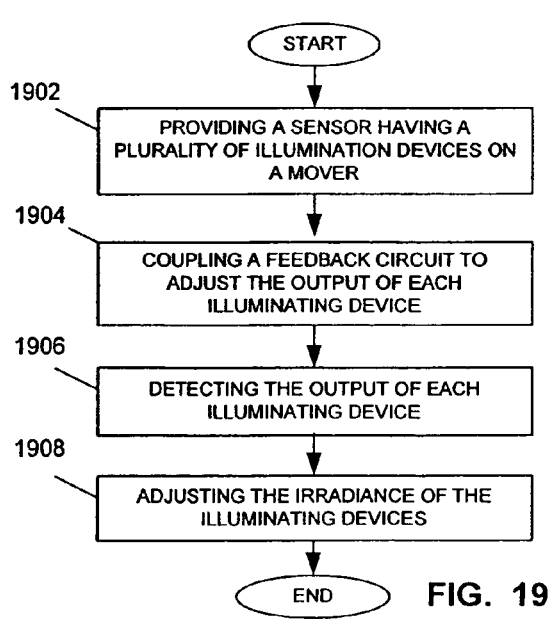
FIG. 19 is a flow chart showing a method of detecting the condition of a turf grass by providing light sources having even weighting according to the present invention.

FIG. 19 is a flow chart showing a method of detecting the condition of a turf grass by providing light sources having even weighting according to the present invention. In particular, a plurality of illuminating devices is provided at a step 1902. A feedback circuit to adjust the output of the illuminating devices coupled to the plurality of illuminating devices at a step 1904. The irradiance of the plurality of illuminating devices is detected at a step 1906. Finally, the irradiance of one or more illuminating devices is adjusted at a step 1908.

Figure 20:
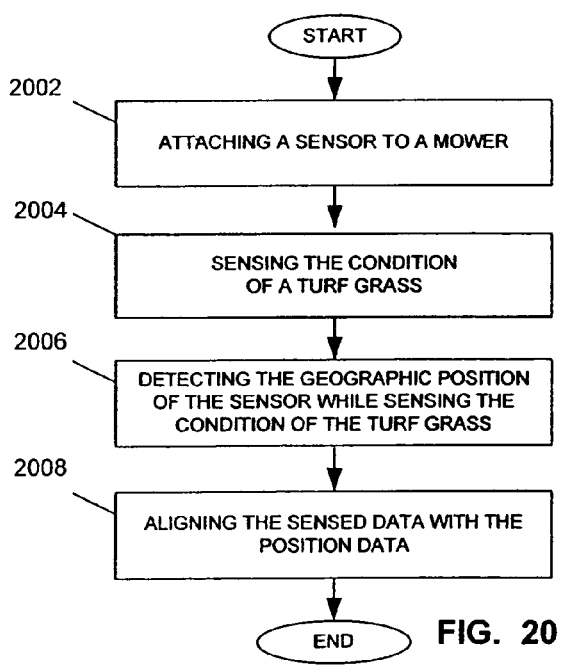
FIG. 20 is a flow chart showing a method of detecting the condition of a turf grass by aligning sensed data with position data according to the present invention.

FIG. 20 is a flow chart showing a method of detecting the condition of a turf grass by aligning sensed data with position data according to the present invention. In particular, a sensor is attached to a step 2002. The condition of the turfgrass is assessed at a step 2004. The geographic position of the sensor is detected while sensing the condition of the turfgrass at a step 2006. The sensed data and position data is aligned at a step 2008.

It can therefore be appreciated that the new and novel turf sensor and method of detecting the condition of a turf grass has been described. It will be appreciated by those skilled in the art that, particular the teaching herein, numerous alternatives and equivalents will be seen to exist which incorporate the disclosed invention. As a result, the invention is not to be limited by the foregoing embodiments, but only by the following claims.

The invention claimed is:

1. A. device for detecting a condition of turf grass, said device comprising:
    an array of LEDs generating a pattern of illuminating light;
    at least one photodetector receiving a pattern of reflected light which is coincident with said pattern of illuminating light;
    one or more photodetectors that detect stray light from said array of LEDs;
    a feedback loop controlling said array of LEDs based upon stray light from said array of LEDs; wherein said feedback loop comprises more than one demodulator for more than one frequency;
    a circuit for providing offset correction, said circuit comprising a first offset correction circuit for a first frequency and a second offset correction circuit for a second frequency; and
    a background light subtraction circuit.

* * * * *

UNITED STATES PATENT AND TRADEMARK OFFICE
CERTIFICATE OF CORRECTION

| | | |
|---|---|---|
| PATENT NO. | : 7,929,141 B2 | Page 1 of 1 |
| APPLICATION NO. | : 12/008402 | |
| DATED | : April 19, 2011 | |
| INVENTOR(S) | : David Franzen et al. | |

It is certified that error appears in the above-identified patent and that said Letters Patent is hereby corrected as shown below:

Title Page,
Please insert the Priority Claim

--This application is a continuation of U.S. Patent Application No. 10/655,748, filed September 5, 2003, now U.S. Pat. No. 7,362,439.--

Signed and Sealed this
Thirteenth Day of December, 2011

David J. Kappos
*Director of the United States Patent and Trademark Office*